United States Patent [19]

Chamberlin, Sr.

[11] Patent Number: Plant 5,297

[45] Date of Patent: Oct. 23, 1984

[54] PEACH TREE, BERENDA SUN

[75] Inventor: Thomas O. Chamberlin, Sr., Visalia, Calif.

[73] Assignee: H. P. Metzler & Sons, Inc., Del Rey, Calif.

[21] Appl. No.: 462,991

[22] Filed: Jan. 27, 1983

[51] Int. Cl.[3] ..... A01H 5/03

[52] U.S. Cl. ..... Plt./43

[58] Field of Search ..... Plt./43

*Primary Examiner*—Robert E. Bagwill

*Attorney, Agent, or Firm*—Huebner & Worrel

[57] ABSTRACT

A peach tree, denominated "Berenda Sun", producing freestone fruit having a dark red color with bright yellow, very crisp and firm flesh and a skin which is tenacious to the flesh ripening July 22 to July 24 in the San Joaquin Valley of California.

1 Drawing Figure

BACKGROUND OF THE VARIETY

The present invention relates to a new and distinct variety of peach tree, denominated "Berenda Sun", broadly characterized by its full freestone fruit and firm and crisp, bright yellow flesh, and more particularly to such a peach tree wherein the fruit has a skin which is tenacious to the flesh and which ripens for picking in the San Joaquin Valley of California about July 22 through 24 and before the patented O'Henry peach.

The commercial value and marketability of fresh fruit, and particularly that of peaches, are intimately related to the physical characteristics of such fruit which allow the fruit to be picked, packed, and handled during shipment without damage to or impairment of the appearance and quality of the fruit. The value of such fruit is also greatly enhanced where it possesses qualities such as to permit storage for substantial periods of time. The fruit of the O'Henry peach tree, covered by U.S. Plant Pat. No. 2,964, possesses good qualities in many of these respects.

The variety of the present invention produces fruit having a tough skin and very crisp flesh and, hence, the fruit is of excellent shipping quality. The fruit is further characterized by its color, ranging from very dark red to bright yellow red to yellow, which affords the fruit an attractive and desirable appearance and consequently an enhanced market value in comparison with the fruit of other varieties. The fruit of the present invention is further characterized by its bright yellow flesh, which ripens evenly and about July 22 through 24. Thus, the fruit of the present variety possesses many of the best commercial features of the O'Henry peach, but is distinct therefrom in a number of significant respects including that it ripens before the O'Henry peach.

ORIGIN AND ASEXUAL REPRODUCTION OF THE NEW VARIETY

The instant new variety of peach tree was discovered by myself in 1976 and is a newly found seedling of the patented O'Henry peach tree. Seeds of the O'Henry peach tree were planted in a plot in the nursery of H. P. Metzler & Sons, Inc. at 5286 South Del Rey Ave., Del Rey, Calif. 93616 in 1974. The first fruit of the present variety was observed in 1976, and its distinctive and superior characteristics were discovered at that time. The present variety was asexually reproduced under my direction at H. P. Metzler & Sons, Inc. in the winter of 1976 to 1977 by grafting several seedlings and setting them out in the test nursery of H. P. Metzler & Sons, Inc. Additional trees were budded later and all of the trees of the instant variety were then set out in a test block of the nursery at Del Rey, Calif. Since that time, the trees of the instant variety, including the parent tree, have been observed and compared, the fruit and tree characteristics resulting from the asexual reproduction proving to be identical to those characteristics exhibited by the original seedling of the new variety.

SUMMARY OF THE NEW VARIETY

The instant variety of peach tree is characterized by its full freestone fruit having a dark red color with very firm, crisp yellow flesh and skin which is tenacious to the flesh, the flesh having a right red rim at the pit cavity, and ripening between July 22 and 24.

BRIEF DESCRIPTION OF THE DRAWING

The accompanying drawing is a color photograph of five mature fruit of the variety of the present invention, one positioned to show the stem end, a second positioned to show the side, a third positioned to show the apex, a fourth sliced along the suture plane with the pit left in place and a fifth sliced along the suture plane with the pit removed to expose the pit cavity. Also shown in the photograph is a representative twig with characteristic leaves.

DETAILED DESCRIPTION

Referring more specifically to the pomological details of this new and distinct variety of peach tree, the following characteristics were observed under the ecological conditions prevailing at the nursery of H. P, Metzler & Sons, Inc. at Del Rey, Fresno County, Calif. and the following is a detailed description of these characteristics.

All major color code plate identifications are by reference to the Color Name Chart of the Inter-Society Color Council, National Bureau of Standards.

TREE

Size: Normal.

Vigor: Very vigorous.

Productivity: Very good.

Regularity of bearing: Bears well every year.

Trunk: Normal peach trunk surface with small lenticels, 12–15 per square inch, and a dark brown color (62 d.g.y. Br.).

Branches: Normal size with small lenticels, 2–15 per square inch, and a dark brown color (62 d.g.y. Br.).

Leaves:

*Length.*—Average 7 inches (17.78 cm).

*Width.*—Average 1¾ inches (4.445 cm).

*Shape.*—Lanceolate.

*Margin.*—Serrate.

*Color.*—Upper side — 127 gy O1G. Lower side — 122 gy Y.G.

*Petiole.*—About ⅝ inch (1.5875 cm) in length. About 3/16 inch (0.47625 cm) in width.

*Stem glands.*—Reinform, with two very small ones opposed at base of leaf; color, 107 m o 1.

Flower buds:

*Size.*—Small.

*Length.*—9/16 Inch (1.42875 cm).

*Diameter.*—5/16 Inch (0.79375 cm).

*Shape.*—Round to slightly elongated. Stamen exposed 3/16 inch (0.47625 cm) before bud opens.

Flowers:

*Date of bloom.*—About Mar. 9th.

*Size.*—Diameter: ¼ inch (0.635 cm). Length of Petal: 7/16 inch (1.11125 cm).

*Color.*—Dark pink (#3 deep pink) outer edge; center 4-1 pink.

FRUIT

Maturity: About July 22nd to July 24th in the San Joaquin Valley of California.

Size:

*Diameter.*—2¾ Inches (6.985 cm) to 3½ inches (8.890 cm).

*Uniformity.*—Good.

*Dimension in suture plane.*—2¾ Inches (6.985 cm) to 3 inches (7.62 cm).

*Dimension in plane normal to suture plane.*—2¾ Inches (6.985 cm) to 3½ inches (8.890 cm).

Form:

*Uniformity.*—Good.

*Symmetry.*—Good.

*Suture.*—Smooth and very slight, extending from base to apex, about 5¼ inches (13.335 cm).

*Ventral surface.*—Rounded to slightly flat.

*Stem cavity.*—Rounded, 1 inch (2.54 cm) wide, ⅝ inch (1.5875 cm) deep.

*Base.*—Wide, slightly flat.

*Apex.*—Rounded to slightly flat.

*Pistil point.*—Very small, slightly receded.

Stem:

*Length.*—7/16 Inch (1.11125 cm).

*Width.*—3/16 Inch (0.47625 cm).

Skin:

*Thickness.*—Medium.

*Texture.*—Smooth, tough texture and tenacious to flesh.

*Tendency to crack.*—None.

*Pubescence.*—Light.

*Color.*—Very dark red (17 V.D. Red) to bright yellow red (13 deep red) to yellow (83 brill yellow).

Flesh.

*Color.*—83 Brill y.

*Surface of pit cavity.*—Rough with ridges showing.

*Color of pit well.*—11 V red.

*Aroma.*—Slight.

*Juice.*—Good, with good flavor.

*Flavor.*—Good, pleasant taste, sweet, very little acid taste.

*Fibers.*—Not fibrous.

*Ripening.*—Even.

*Eating quality.*—Very firm and crisp with good flavor.

Stone:

*Type.*—Freestone.

*Fibers.*—None.

*Size.*—Length: 1⅜ Inches (3.4925 cm). Width: 1-1/16 inches (2.69875 cm). Thickness: 1-1/16 inches (2.69875 cm) to 1⅛ inches (2.8575 cm).

*Form.*—Normal peach pit, rough with ridges running on longitudinal axes. Stem end flat, apex pointed. Slight ridge on base side with substantial ridge on top side from base to apex.

*Color.*—58 Med. Brown.

*Ridges.*—1/16 Inch (0.15875 cm) or less in height.

*Tendency to split.*—None.

Use: Fresh market.

*Keeping quality.*—Very good. Has been kept in storage more than four weeks without deterioration.

*Shipping quality.*—Very good, due to tough skin and very crisp flesh.

Although the new variety of peach tree possesses the described characteristics as a result of the growing conditions in Fresno County, Calif., in the central portion of the San Joaquin Valley, it is to be understood that variations of the magnitude and characteristics incident to growing conditions, fertilization, pruning, pest control, and other horticultural practices are to be expected.

Having thus described and illustrated my new variety of peach tree, what is new and desired to be secured by Letters Patent is:

1. A new and distinct variety of peach tree substantially as illustrated and described and which is characterized by its freestone fruit having a dark red color with bright yellow flesh of very firm and crisp character with a bright red rim bounding the pit cavity and by its skin which is tough and tenacious to the flesh, and ripening about July 22 through July 24.

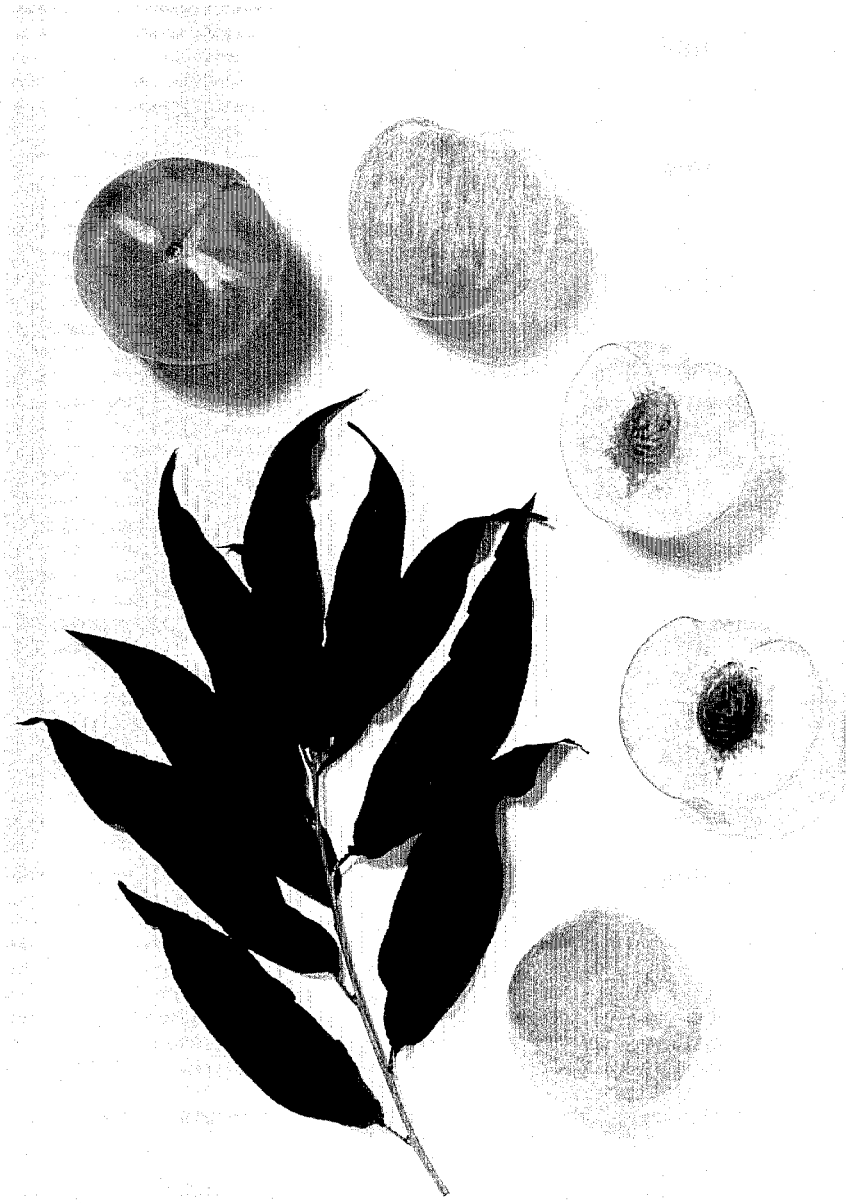

* * * * *